(12) United States Patent
Saulnier et al.

(10) Patent No.: US 9,005,666 B2
(45) Date of Patent: Apr. 14, 2015

(54) PROCESS FOR PREPARING LIPID NANOPARTICLES

(75) Inventors: Patrick Saulnier, Marigne (FR); Jean-Pierre Benoit, Angers (FR); Nicolas Anton, Strasbourg (FR)

(73) Assignees: L'Universite d'Angers, Angers (FR); Inserm Transfert, Paris (FR)

( * ) Notice: Subject to any disclaimer, the term of this patent is extended or adjusted under 35 U.S.C. 154(b) by 942 days.

(21) Appl. No.: 12/663,960

(22) PCT Filed: Jun. 11, 2008

(86) PCT No.: PCT/FR2008/051043
§ 371 (c)(1), (2), (4) Date: May 24, 2010

(87) PCT Pub. No.: WO2009/004214
PCT Pub. Date: Jan. 8, 2009

(65) Prior Publication Data
US 2010/0233275 A1 Sep. 16, 2010

(30) Foreign Application Priority Data
Jun. 11, 2007 (FR) ..................................... 07 55662

(51) Int. Cl.
| | |
|---|---|
| *A61K 9/16* | (2006.01) |
| *A61K 9/50* | (2006.01) |
| *A61K 9/51* | (2006.01) |
| *A61K 9/107* | (2006.01) |
| *A61K 31/192* | (2006.01) |
| *A61K 31/70* | (2006.01) |

(52) U.S. Cl.
CPC ............. *A61K 9/5123* (2013.01); *A61K 9/1075* (2013.01); *A61K 31/192* (2013.01); *A61K 31/70* (2013.01)

(58) Field of Classification Search
None
See application file for complete search history.

(56) References Cited

U.S. PATENT DOCUMENTS

| | | | |
|---|---|---|---|
| 6,241,969 B1 * | 6/2001 | Saidi et al. ...................... 424/45 |
| 2003/0152635 A1 * | 8/2003 | Heurtault et al. ............. 424/490 |
| 2004/0076683 A1 | 4/2004 | Hoarau et al. |

FOREIGN PATENT DOCUMENTS

| | | |
|---|---|---|
| EP | 1 265 698 | 6/2004 |
| EP | 1 955 695 A1 | 8/2008 |
| FR | 2 805 761 | 9/2001 |
| FR | 2 840 532 A1 | 12/2003 |

OTHER PUBLICATIONS

U.S. Appl. No. 13/139,401, filed Jun. 13, 2011, Benoit, et al.
Lamprecht, Alf et al. "Etoposide nanocarriers suppress glioma cell growth by intracellular drug delivery and simultaneous P-glycoprotein inhibition", Journal of Controlled Release, Elsevier, vol. 112, No. 2, pp. 208-213, May 15, 2006.
U.S. Appl. No. 13/260,168, filed Sep. 23, 2011, Benoit, et al.
U.S. Appl. No. 12/663,937, filed Dec. 10, 2009, Saulnier, et al.
Roberta Cavalli et al., "Effects of Some Experimental Factors on the Production Process of Solid Lipid Nanoparticles", 6104 European Journal of Pharmaceutics and Biopharmaceutics, No. 2, XP-000582516, Apr. 1996, pp. 110-115.

* cited by examiner

*Primary Examiner* — Michael B Pallay
(74) *Attorney, Agent, or Firm* — Oblon, McClelland, Maier & Neustadt, L.L.P.

(57) ABSTRACT

A process for preparing nanocapsules with a liquid lipid core and a solid lipid shell, charged with at least one active agent. The process contains at least the steps of formulating a microemulsion by phase inversion of an emulsion, totally or partially forming from at least one active agent a second composition different than the microemulsion, placing the microemulsion in contact with the second composition under conditions suitable for interaction of the active agent with the microemulsion, and chill-hardening the microemulsion that has interacted with the active agent, to obtain the nanocapsules.

19 Claims, 2 Drawing Sheets

PROCESS FOR PREPARING LIPID NANOPARTICLES

The present invention is directed toward proposing a kit that is useful for extemporaneously preparing lipid nanocapsules charged with at least one active agent, and is also directed toward proposing a process that is useful for preparing such nanocapsules.

Nanovesicular systems, of nanocapsule or nanodroplet type whose size ranges from 50 to 500 nanometers and which are formed from a liquid or solid core surrounded by an outer membrane, are already known. The constituents of their membrane may be synthetic, for example of polymeric, protein or lipid nature like liposomes. In particular, liposomes that have a lamellar structure formed from a stack of lipid layers separated from each other by aqueous compartments always have an aqueous core.

These nanometric structures have also already been proposed for the purposes of encapsulating active agents either in their aqueous core when the active agent is water-soluble or water-dispersible, or in their lipid layer when the active agent is liposoluble or lipodispersible.

For example, U.S. Pat. No. 5,961,970 proposes, as active agent vehicles, oil-in-water emulsions at the submicron scale, i.e. miniemulsions whose droplets have a hydrophobic core of lipid nature and are surface-stabilized with amphiphilic and/or nonionic surfactants like surfactants of phospholipid type. These droplets are thus maintained in suspension in an aqueous phase. This type of submicron emulsion is obtained from a basic emulsion by subjecting it to several successive homogenization cycles at high shear.

U.S. Pat. No. 5,576,016 describes macroemulsions whose droplets are formed from a solid lipid core and which are stabilized with a phospholipid envelope. This phospholipid envelope has a lamellar structure formed from one or more layers of phospholipid molecules like liposomes. A highly hydrophobic active agent may be charged into the nucleus, and a water-soluble active agent may, on the other hand, be incorporated into the aqueous compartments present in the phospholipid envelope.

Moreover, the inventors have also described in patent EP 1 265 698, as vehicles for liposoluble or lipodispersible active agents, nanocapsules with a liquid core and a solid shell of lipid nature, and novel technology for gaining access thereto. More specifically, these nanocapsules charged with liposoluble or lipodispersible active agents are obtained from a microemulsion, this microemulsion being prepared via the technique of phase inversion via a thermal effect (PIT emulsion).

The principle of phase inversion temperature (PIT) emulsification is well known to those skilled in the art; it was described in 1968 by K. Shinoda (J. Chem. Soc. Jpn, 1968, 89, 435). It was shown that this emulsification technique makes it possible to obtain fine stable emulsions (K. Shinoda and H. Saito, J. Colloid Interface Sci., 1969, 30, 258).

The principle of this technique is as follows: an emulsion, for example a W/O emulsion, is prepared at a temperature that must be higher than the phase inversion temperature of the system, i.e. the temperature at which the equilibrium between the hydrophilic and lipophilic properties of the surfactant system used is reached. At high temperature, i.e. above the phase inversion temperature (>PIT), the emulsion is of water-in-oil type, and, during its cooling, this emulsion becomes inverted at the phase inversion temperature, to become an emulsion of oil-in-water type, and does so by proceeding beforehand through a microemulsion state. This technique makes it possible especially to gain access to a mean size of the globules constituting the oily phase ranging from 0.1 to 4 μm (100 to 4000 nm).

However, when these nanocapsules are intended for encapsulating an active agent, this process demands the availability, from its very first step, of the active material that it is desired to encapsulate and thus demands that the entire process be performed in the presence of this active agent. However, this obligation may occasionally be burdensome to a person skilled in the art.

Thus, a person skilled in the art does not have available a method that is quick and easy to implement for gaining access to nanocapsules charged with active agents. Moreover, such a process does not permit the use of heat-sensitive active agents.

The present invention is directed precisely toward proposing a novel process that can overcome the abovementioned drawbacks.

More precisely, according to a first of its aspects, the present invention is directed toward a process that is useful for preparing nanocapsules with a liquid lipid core and a solid lipid shell, charged with at least one active agent, said process comprising at least the steps consisting in:

having a microemulsion, which is thus in a nonsolid state, formulated or formed by phase inversion of an emulsion and stabilized with at least one surfactant system containing at least one hydrophilic, nonionic, heat-sensitive surfactant and, where appropriate, a lipophilic surfactant, having a second composition, different than said microemulsion and totally or partially formed from at least one active agent, placing said microemulsion in contact with said second composition under conditions suitable for interaction of said active agent with said microemulsion, and chill-hardening said microemulsion that has interacted with said active agent, so as to obtain nanocapsules comprising said active agent and formed from a lipid core that is liquid at room temperature, coated with a lipid film that is solid at room temperature.

According to another of its aspects, the present invention is directed toward a kit that is useful for the preparation of nanocapsules with a liquid lipid core and a solid lipid shell, charged with at least one active agent, which is especially water-soluble, water-dispersible, liposoluble or lipodispersible, said kit comprising at least:

a first composition comprising at least one oily fatty phase, one aqueous phase and one surfactant system comprising at least one nonionic, hydrophilic, heat-sensitive surfactant and, where appropriate, a lipophilic surfactant, said first composition being in the form of a microemulsion formed by phase inversion of an emulsion, and a second composition, separate from the first composition, comprising at least one active agent, which is especially water-soluble, water-dispersible, liposoluble or lipodispersible.

A surfactant system that is especially suitable for a kit of the invention is more particularly described hereinbelow.

Such a kit is especially advantageous insofar as it offers its user the possibility of extemporaneously producing in a simplified manner nanocapsules charged with at least one active agent.

According to one embodiment variant, said kit may contain several second compositions that differ than each other at least in the nature of the active agent they contain.

According to yet another of its aspects, the present invention is directed toward the use of a kit according to the invention for extemporaneously preparing nanocapsules with a liquid lipid core and a solid lipid shell, charged with at least one active agent.

The present invention results more particularly from the observation by the inventors that, contrary to all expectation, a microemulsion obtained by phase inversion of an emulsion, in particular according to the phase inversion temperature technique, proves to be endowed with a capacity to interact with an active agent so as either to encapsulate it inside these nanodroplets of oily phase, or to adsorb it in the lipid shell of these droplets. Surprisingly, this interaction does not affect the stability of the microemulsion.

Microemulsion

Firstly, it is important to note that a microemulsion is different than a miniemulsion and than a macroemulsion especially as illustrated in U.S. Pat. No. 5,961,971 and U.S. Pat. No. 5,576,016. Specifically, a microemulsion corresponds to bi-continuous structuring of the material in the form of micellar structures swollen with oil or water. These micellar structures are highly mutually interlinked, and thus constitute a homogeneous, cohesive, stabilized three-dimensional network. In other words, it is not possible to distinguish the dispersed phase from the continuous phase. This microemulsion is in thermodynamic equilibrium, and can therefore exist only under very specific temperature, pressure and composition conditions.

As stated previously, the microemulsion may comprise at least one oily fatty phase, one aqueous phase and one surfactant system comprising at least one heat-sensitive, hydrophilic, nonionic surfactant and preferably in combination with at least one lipophilic surfactant.

a—Oily Fatty Phase

The oily fatty phase is formed from at least one fatty substance that is liquid or semiliquid at room temperature, and in particular from at least one triglyceride or fatty acid ester, or a mixture thereof.

The fatty acid ester may be chosen more particularly from $C_8$ to $C_{18}$ and especially $C_8$ to $C_{12}$ fatty acid esters and especially ethyl palmitate, ethyl oleate, ethyl myristate, isopropyl myristate and octyldodecyl myristate, and mixtures thereof.

The triglycerides used may be synthetic triglycerides or triglycerides of natural origin. The natural sources may include animal fats or plant oils, for example soybean oils or sources of long-chain triglycerides (LCT).

Other triglycerides of interest are composed mainly from medium-length fatty acids, also known as medium-chain triglycerides (MCT). A medium-chain triglyceride (MCT) oil is a triglyceride in which the hydrocarbon chain contains from 8 to 12 carbon atoms.

Such MCT oils are commercially available.

As examples of these MCT oils, mention may be made of the TCR products (commercial name from the Société Industrielle des Oléagineux, France, for a triglyceride mixture in which about 95% of the fatty acid chains contain 8 or 10 carbon atoms) and Miglyol® 812 (triglyceride sold by the company Dynamit Nobel, Sweden, for a mixture of caprylic and capric acid glyceride triesters).

The fatty acid units of these triglycerides may be unsaturated, monounsaturated or polyunsaturated. Mixtures of triglycerides containing variable fatty acid units are also acceptable.

It should be noted that the higher the HLB value of the liquid or semiliquid fatty substance, the higher the phase inversion temperature. On the other hand, the HLB value of the fatty substance does not appear to have an influence on the size of the nanocapsules.

Thus, when the size of the end groups of the triglycerides increases, their HLB value decreases and the phase inversion temperature decreases.

The HLB value, or hydrophilic-lipophilic balance, is defined by C. Larpent in Traité K.342 of the Editions Techniques de l'Ingénieur.

The triglyceride sold under the name Labrafac WL 1349® is most particularly suitable for use in the invention.

b—Surfactant System

This surfactant system comprises at least one heat-sensitive, hydrophilic, nonionic surfactant.

The heat-sensitive, hydrophilic, nonionic surfactant used according to the present invention is advantageously an amphiphilic hydrophilic surfactant.

The emulsifying surfactants usually used have an HLB (HLB=Hydrophilic-Lipophilic Balance) value ranging from 8 to 18. These emulsifiers, by virtue of their amphiphilic structure, position themselves at the oily phase/aqueous phase interface and thus stabilize the droplets of dispersed oils.

Thus, the surfactant system used in the microemulsion may comprise one or more surfactants whose solubility in the oil increases as the temperature increases. The HLB of these surfactants may range from 8 to 18 and preferably from 10 to 16, and these surfactants may be chosen from ethoxylated fatty alcohols, ethoxylated fatty acids, partial glycerides of ethoxylated fatty acids and polyethoxylated fatty acid triglycerides, and mixtures thereof.

Examples of ethoxylated fatty alcohols that may be mentioned include adducts of ethylene oxide with lauryl alcohol, especially those comprising from 9 to 50 oxyethylene groups (Laureth-9 to Laureth-50 in CTFA names); adducts of ethylene oxide with behenyl alcohol, especially those comprising from 9 to 50 oxyethylene groups (Beheneth-9 to Beheneth-50 in CTFA names); adducts of ethylene oxide with cetostearyl alcohol (mixture of cetyl alcohol and stearyl alcohol), especially those comprising from 9 to 30 oxyethylene groups (Ceteareth-9 to Ceteareth-30 in CTFA names); adducts of ethylene oxide with cetyl alcohol, especially those comprising from 9 to 30 oxyethylene groups (Ceteth-9 to Ceteth-30 in CTFA names); adducts of ethylene oxide with stearyl alcohol, especially those comprising from 9 to 30 oxyethylene groups (Steareth-9 to Steareth-30 in CTFA names); adducts of ethylene oxide with isostearyl alcohol, especially those comprising from 9 to 50 oxyethylene groups (Isosteareth-9 to Isosteareth-50 in CTFA names); and mixtures thereof.

Examples of ethoxylated fatty acids that may be mentioned include the adducts of ethylene oxide with lauric, palmitic, stearic or behenic acid, and mixtures thereof, especially those comprising from 9 to 50 oxyethylene groups, such as PEG-9 to PEG-50 laurates (CTFA names: PEG-9 laurate to PEG-50 laurate); PEG-9 to PEG-50 palmitates (CTFA names: PEG-9 palmitate to PEG-50 palmitate); PEG-9 to PEG-50 stearates (CTFA names: PEG-9 stearate to PEG-50 stearate); PEG-9 to PEG-50 palmitostearates; PEG-9 to PEG-50 behenates (CTFA names: PEG-9 behenate to PEG-50 behenate); and mixtures thereof.

Mixtures of these oxyethylenated derivatives of fatty alcohols and of fatty acids may also be used.

These surfactants may also be either natural compounds such as echolate phospholipids or synthetic compounds such as polysorbates, which are polyethoxylated fatty acid esters of sorbitol (Tween®), polyethylene glycol esters of a fatty acid originating, for example, from castor oil (Cremophor®), polyethoxylated fatty acids, for example stearic acid (Simulsol M-53®), polyoxyethylenated fatty alcohol ethers (Brij®), polyoxyethylenated nonphenyl ethers (Triton N®) and polyoxyethylenated hydroxyphenyl ethers (Triton X®).

It may more particularly be a polyethylene glycol 2-hydroxystearate and especially the product sold under the name Solutol® HS15 by the company BASF (Germany).

According to one preferred embodiment, said surfactant system may advantageously also comprise at least one lipophilic surfactant.

Advantageously, the lipophilic surfactant is solid at room temperature.

The lipophilic surfactant is more particularly based on phospholipids that are advantageous with regard to their biocompatible nature.

Among the phospholipids, phosphatidylcholines (lecithin) are particularly advantageous.

Other phospholipids may be phosphatidylglycerol, phosphatidylinositol, phosphatidylserine, phosphatidic acid and phosphatidylethanolamine.

The phospholipid derivatives may be isolated from natural sources or prepared via synthesis.

As commercial products derived from phospholipids, mention may be made more particularly of:

Epicuron 120® (Lukas Meyer, Germany), which is a mixture of about 70% phosphatidylcholine, 12% phosphatidylethanolamine and about 15% other phospholipids;

Ovotine 160® (Lukas Meyer, Germany), which is a mixture comprising about 60% phosphatidylcholine, 18% phosphatidylethanolamine and 12% other phospholipids, a mixture of purified phospholipids such as the products Lipoid E75 or Lipoid E80® (Lipoid, Germany), which is a mixture of phospholipids comprising about 80% by weight of phosphatidylcholine, 8% by weight of phosphatidylethanolamine, 3.6% by weight of nonpolar lipids and 2% of sphingomyelin.

According to one preferred embodiment, the lipophilic surfactant is a lecithin whose proportion of phosphatidylcholine ranges from 40% to 80% by weight.

Lipoid S75-3® (Lipoid GmbH, Germany) is most particularly suitable as a source of phosphatidylcholine. It is soybean lecithin. This product contains about 69% phosphatidylcholine and 9% phosphatidylethanolamine. This constituent is the only constituent that is solid at 37° C. and at room temperature in the formulation.

Polyglyceryl-6 dioleate (Plurol®) may also be used.

The liquid fatty substance/lipophilic surfactant(s) ratio may range from 1 to 15, preferably from 1.5 to 13 and more preferentially from 3 to 8.

It should be noted that the particle size decreases when the proportion of hydrophilic surfactant increases and when the proportion of surfactants (hydrophilic and, where appropriate, lipophilic) increases. Specifically, the surfactant(s) and in particular the hydrophilic surfactant(s) entrain(s) a decrease in the interface tension and thus stabilization of the system, which promotes the production of small particles.

Moreover, the particle size increases when the proportion of oil increases.

For its part, the aqueous phase of the microemulsion may also advantageously contain 1% to 4% of a salt, especially a mineral salt, for instance sodium chloride. Specifically, modification of the salt concentration results in shifting of the phase inversion zone. Thus, the higher the salt concentration, the lower the phase inversion temperature. This phenomenon proves to be most particularly advantageous for the encapsulation of hydrophobic heat-sensitive active principles.

According to one particular embodiment, the microemulsion may thus advantageously contain from 1% to 3% of lipophilic surfactant(s), from 5% to 15% of hydrophilic surfactant(s), from 5% to 15% of an oily phase and from 64% to 89% of an aqueous phase (the percentages are expressed on a weight basis relative to the total weight of the microemulsion).

According to one embodiment, a microemulsion that is suitable for the invention may be formed from at least one fatty acid triglyceride and a polyethylene glycol 2-hydroxystearate derivative, and, where appropriate, a lecithin.

In one preferred embodiment, the fatty phase is a fatty acid triglyceride, the lipophilic surfactant is a lecithin and the hydrophilic surfactant is Solutol® HS15.

A microemulsion that is suitable for use in the invention may especially be accessible according to the phase inversion technique, in particular via a phase inversion temperature operation starting with an emulsion, stabilized with the surfactant system considered for the microemulsion.

A microemulsion that is most particularly suitable for use in the invention is accessible via a phase inversion temperature operation starting with an oil-in-water emulsion.

This sole phase inversion temperature operation, required to obtain the starting microemulsion, may be performed once only or repeated.

This technology is more particularly described in patent EP 1 265 698, the content of which is incorporated into the present patent application.

Thus, all the constituents intended to form the microemulsion are weighed out in a container. The mixture is homogenized, for example using a Rayneri blender at 350 rpm, and heated by gradually raising the temperature using a water bath up to a temperature greater than or equal to the phase inversion temperature $T_2$, i.e. until a more viscous white phase is obtained, which indicates that the inverse emulsion has been obtained. Heating is then stopped and stirring is maintained until the emulsion has cooled to room temperature, passing through the phase inversion temperature $T_1$, i.e. the temperature at which the expected microemulsion forms, in the form of a transparent or translucent phase. When the temperature has fallen below the phase inversion temperature ($T_1$), the starting emulsion is again obtained.

More specifically, the phase inversion between the oil/water emulsion and the water/oil emulsion is reflected by a decrease in conductivity when the temperature increases, until it becomes cancelled out.

Thus, $T_1$ is a temperature at which the conductivity is at least equal to 90-95% of the conductivity measured at 20° C. and $T_2$ is the temperature at which the conductivity cancels out and the inverse emulsion forms. The mean temperature of the phase inversion zone corresponds to the phase inversion temperature (PIT).

In the zone for formation of a microemulsion (translucent mixture), the hydrophilic and hydrophobic interactions are equilibrated since the surfactant system has a tendency to form both direct micelles and inverse micelles. By heating beyond this zone, formation of a W/O emulsion generally takes place (white opaque mixture), since the surfactant promotes the formation of a water-in-oil emulsion. Next, during cooling below the phase inversion zone, the emulsion becomes an O/W emulsion.

Active Agent

For the purposes of the invention, the term "charged with an active agent" means that the nanocapsules obtained after the process according to the invention comprise at least one active agent encapsulated or incorporated in their liquid lipid core and/or adsorbed in their solid lipid shell.

For the purposes of the invention, the term "adsorbed" means that the active agent is incorporated into the shell. This adsorption phenomenon should be distinguished from simple covalent bonding established between a function present on said active agent and a function present on the surface of the shell of the nanocapsules.

The active agent may be water-soluble, water-dispersible, liposoluble or lipodispersible.

According to one embodiment variant, the active agent is water-soluble or water-dispersible. It is then preferably adsorbed into the solid lipid shell of the nanocapsules.

According to another variant, the active agent may be liposoluble or lipodispersible. In such a case, it is preferentially incorporated into the core of the nanocapsules.

According to yet another variant, the active agent may be water-soluble or water-dispersible and may be incorporated in the form of inverse micellar species dispersed in the lipid core of the nanocapsules.

For the purposes of the invention, the expression "inverse micellar system of water-soluble or water-dispersible active agent" denotes an architecture in which the water-soluble or water-dispersible active agents are stabilized in an oily phase via the surfactant molecules or the surfactant system forming the micellar system into which the active agent will be incorporated.

Inverse micellar systems are well known to those skilled in the art and are especially exploited for performing selective extractions of proteins or enzymes of interest.

For obvious reasons, the choice of the surfactant system used to form the inverse micellar system is to be made taking into account the solubility of the surfactant(s) of which it is formed, in the oily phase of the oil-in-water emulsion in which the active agent is precisely intended to be formulated. This selection clearly falls within the competence of a person skilled in the art.

Advantageously, the surfactants that are used for producing these inverse micelles and that are suitable for use in the invention have an HLB value of less than 10 and in particular less than or equal to 6. They may belong, without preference, to the families of ionic, nonionic or amphoteric surfactants.

These surfactants may be used in an active agent(s)/surfactant(s) weight ratio ranging from 0.01 to 0.3 and in particular from 0.05 to 0.1.

Advantageously, these surfactants may be associated with co-surfactants, for instance phospholipids. In this respect, phosphatidylcholines (lecithin) are particularly advantageous.

Other phospholipids suitable for use in the invention may be phosphatidylglycerol, phosphatidylinositol, phosphatidylserine, phosphatidic acid or phosphatidylethanolamine.

In the case of charging several active agents into a nanocapsule, these active agents may be employed in the process according to the invention via second compositions that may or may not be specific thereto.

These different second compositions may also be employed at the same or different stages of variants of the process according to the invention.

The active agent may be a pharmaceutically active or cosmetically active compound or an agent that is active in the plant protection or food sector.

According to one preferred embodiment, this active agent is a pharmaceutically active principle.

The nanocapsules of the invention are more particularly suitable for the administration of the following active principles: anti-infectious agents, including antifungal agents, antibiotics, anticancer agents, immunosuppressants, active principles intended for the central nervous system which must cross the blood-brain barrier, such as antiparkinsonian agents, analgesics and, more generally, active principles for treating neurodegenerative diseases.

As nonlimiting illustrations of water-soluble or water-dispersible active agents that may be encapsulated according to the invention, mention may be made especially of 5-fluorouracil, gemcitabine, doxorubicin and addition salts thereof with a pharmaceutically acceptable acid and more particularly the hydrochloride, and low molecular weight heparins.

As nonlimiting illustrations of liposoluble or lipodispersible active agents that may be encapsulated according to the invention, mention may be made especially of etoposide or ibuprofen.

Such an active agent may also be of protein or peptide nature. It may also be a nucleic acid such as a DNA plasmid or interference RNA.

The active agent may also be a radiopharmaceutical agent. It may also be a gas or a fluid that can be converted into a gas.

According to the invention, this active agent may be formulated in a second composition. This second composition may, for example, contain this active agent in a dissolved form, for example in water or an aqueous medium when the active agent is water-soluble or water-dispersible, or in a liquid fatty substance when this active agent is liposoluble or lipodispersible. Advantageously, the liquid fatty substance may be of the same nature or, failing that, may be chemically compatible with the fatty substance forming the associated microemulsion.

This active agent may also be formulated in a dry form. In this case, it forms the second composition per se.

As stated previously, the active agent is placed in contact with said microemulsion under conditions that are suitable for their interaction.

Process According to the Invention

In the process according to the present invention, the starting microemulsion is advantageously not charged with active agent.

The microemulsion that has interacted with the active agent(s) according to the claimed process is subsequently subjected to chill-hardening according to the invention.

This step for forming the nanocapsules according to the invention consists of sudden cooling of the microemulsion to a temperature suitable for solidification of the interfacial films composing the microemulsion. This temperature is generally very much below $T_1$. The cooling is advantageously performed with magnetic stirring.

For example, chill-hardening of said microemulsion charged with one or more active agents may be performed at a temperature at least 30° C. below the PIT at the time of the chill-hardening.

This chill-hardening may be performed by diluting the medium 3- to 10-fold with deionized water at 2° C.±1° C. thrown into the fine microemulsion. The nanocapsules obtained are then kept stirring for 5 minutes.

The organization of the system in the form of nanocapsules after chill-hardening is reflected visually by a change in the appearance of the initial system, which changes from opaque-white to translucent-white with a Tyndall effect (bluish tints). This change takes place at a temperature below the PIT. This temperature is generally between 6 and 15° C. below the PIT.

In one embodiment variant, the process according to the invention may also comprise at least one phase inversion temperature step advantageously brought about by a temperature rise and fall imposed on the microemulsion.

This embodiment variant is advantageous in several respects. Thus, it has been found that during the temperature cycles, the shell of the nanoparticles that form after chill-hardening advantageously becomes thicker and thus more stable.

Furthermore, it should be noted that the temperature of the phase inversion zone has a tendency to decrease gradually in the course of the imposed temperature cycles. This phenomenon is precisely advantageous when the active agent that it is desired to encapsulate or adsorb is a temperature-sensitive active agent. Under such conditions, introduction of the active agent at the time of a temperature-compatible cycle is favored.

More specifically, before the chill-hardening intended to form the nanocapsules charged with at least one active agent, the microemulsion under consideration according to the invention, optionally charged with at least one active agent, is successively subjected at least to the steps consisting in:

increasing its temperature up to a temperature $T_2$ above its phase inversion temperature (PIT) to obtain a water-in-oil emulsion, followed by decreasing the temperature to a temperature $T_1$, $T_1$<PIT<$T_2$ to again obtain an oil-in-water emulsion, where appropriate, performing one or more temperature cycles around the phase inversion zone between $T_1$ and $T_2$ and stabilizing said system at a temperature that is in or close to the phase inversion zone to form a new microemulsion obtained via phase inversion.

Thus, one or more temperature cycles may advantageously be performed around the phase inversion zone between $T_1$ and $T_2$, until a translucent suspension is observed, which corresponds to the formation of a new microemulsion. The system is then stabilized at a temperature that corresponds to the structuring of the system as the new expected microemulsion.

The number of cycles applied to the microemulsion depends on the amount of energy required to form the nanocapsules.

This or these phase inversion temperature step(s) may be performed before or after placing said microemulsion in contact with said second composition.

More particularly, the starting microemulsion is not formed in situ, i.e. it is not formed in the presence of the composition containing the active agent.

According to one embodiment variant, the microemulsion of step 1 may undergo, prior to being placed in contact with said second composition, at least one phase inversion temperature step as defined above.

According to another embodiment variant, the microemulsion of step 1 may, after having interacted with said second composition, undergo at least one phase inversion temperature step as defined above.

After the process according to the invention, nanocapsules charged with at least one active agent are obtained.

For the purposes of the invention, the term "nanocapsules" should be distinguished from nanospheres. The term "nanocapsules" means particles formed from a core that is liquid or semiliquid at room temperature, coated with a film or shell that is solid at room temperature, as opposed to nanospheres, which are matrix particles, i.e. all of the mass is solid. Thus, when nanospheres contain a pharmaceutically active principle, it is finely divided in the solid matrix.

Figure 1:
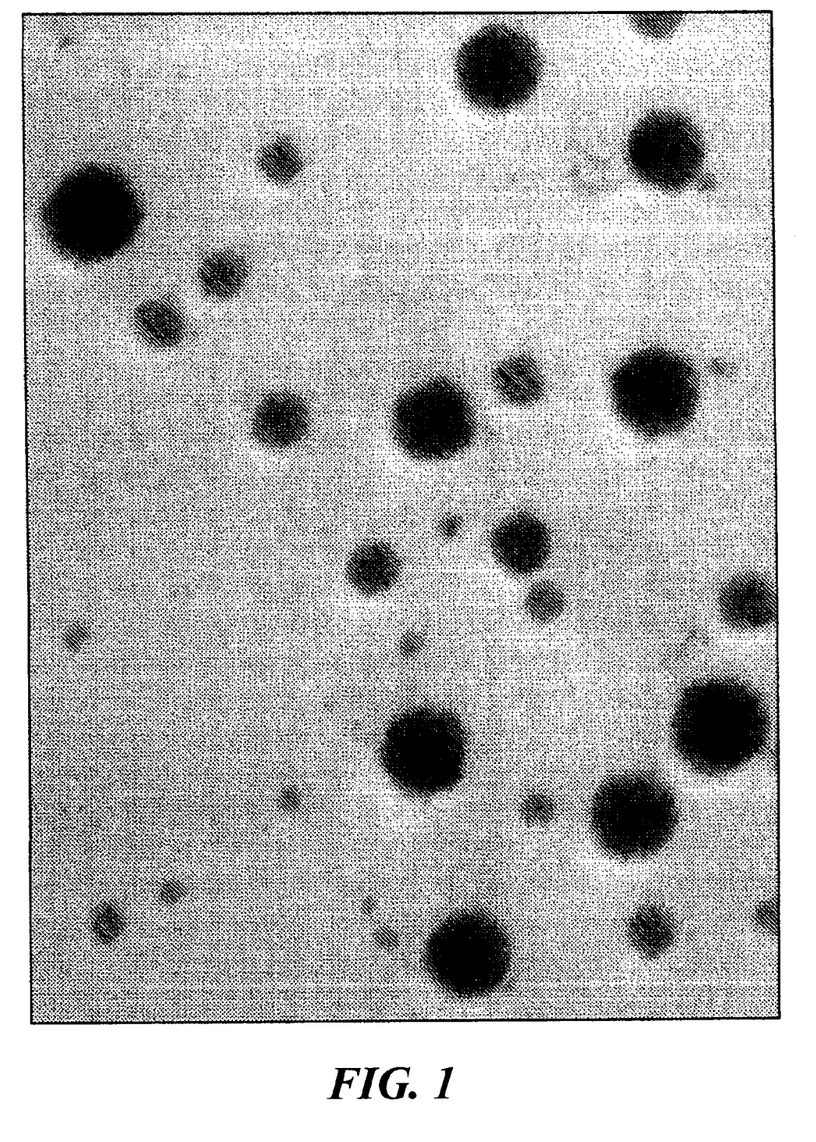
FIG. 1 is a photograph of a sample of nanocapsules about 90 nm in size, visualized by transmission electron microscopy (TEM) after staining with osmium tetroxide (size measured by light scattering).

Advantageously, the nanocapsules obtained according to the invention have a mean size of less than 150 nm, preferably less than 100 nm and more preferably less than 50 nm. These sizes may be determined by photon correlation spectroscopy, scanning electron microscopy, or transmission electron microscopy in cryoscopic mode. By way of illustration, FIG. 1 is a photograph obtained by TEM showing a sample of nanocapsules about 90 nm in size.

The thickness of the solid film or shell is advantageously between 2 and 10 nm. It is also about a tenth of the diameter of the particles. This thickness may be calculated via the mass balance, or visualized by negative-shadow transmission electron microscopy or alternatively by transmission electron microscopy in cryoscopic mode.

Given their size, the nanocapsules of the invention are colloidal lipid particles.

The polydispersity index of the nanocapsules of the invention is advantageously between 5% and 15%. This index is determined on the size histogram obtained via the photon correlation spectroscopy method.

The nanocapsules are each formed from an essentially lipid core that is liquid or semiliquid at room temperature, coated with an essentially lipid shell that is solid at room temperature.

For the purposes of the invention, the term "essentially lipid" means that the core and the shell forming the nanocapsules according to the invention are formed from more than 50% by weight, in particular more than 75% by weight, especially more than 80% by weight, or even more than 90% and more particularly more than 95% of their respective weight, or even totally, from one or more lipid (hydrophobic) compounds.

For the purposes of the invention, the term "room temperature" denotes a temperature ranging from 18 to 25° C.

The present invention is illustrated by the examples that follow, which are given as nonlimiting illustrations of the field of the invention.

EXAMPLE 1

Preparation of a Microemulsion not Charged with Active Agent 5 g of an emulsion containing 75 mg of Lipoid S75-3®, 504 mg of lipophilic Labrafac WL 1349®, 504 mg of Solutol HS®, 15.383 g of water and 88 mg of sodium chloride are prepared.

The whole is placed in the same beaker under magnetic stirring. Heat is applied until a temperature of 85° C. is reached. With continued magnetic stirring, the system is allowed to cool to a temperature of 60° C. These heating cycles (between 85° C. and 60° C.) are performed three times so as to obtain microemulsions that are more and more structured. The system is then maintained in its microemulsion form by stabilizing it at a temperature that is within (or close to) the phase inversion zone, in the present case 65° C.

EXAMPLE 2

Preparation of Nanocapsules Charged with Active Agent Using the Microemulsion of Example 1

The formation of the microemulsion obtained by phase inversion remains strictly identical to that described previously. In this Example 2, 10 mg of an anticancer lipophilic active agent (etoposide) in powder form are dissolved in the Labrafac (500 mg). The composition containing the active agent (2 ml) is added to the microemulsion described in Example 1. The nanocapsules are finished by chill-hardening in cold water (5° C.).

The nanocapsules charged with active principle are separated from the medium by centrifugation.

A degree of incorporation of 95% by weight of active agent is confirmed via an adapted HPLC method (Alf Lamprecht, Jean-Pierre Benoit, Etoposide nanocarriers suppress glioma cell growth by intracellular drug delivery and simultaneous P-glycoprotein inhibition, Journal of Controlled Release 112 (2006) 208-213).

EXAMPLE 3

Preparation of Nanocapsules Charged with Active Agent Using the Microemulsion of Example 1

The formulation of the nanocapsules remains strictly identical to that described in Example 1. In this case, 100 mg of ibuprofen are predissolved in the 504 mg of Labrafac. This preparation is placed in contact with the other constituents at the very start of formulation. The nanocapsules charged with active principle are separated from the medium by centrifugation.

The ibuprofen is assayed via an HPLC method according to the protocol described in Alf Lamprecht et al. (Lipid nanocarriers as drug delivery system for ibuprofen in pain treatment, International Journal of Pharmaceutics 278 (2004) 407-414). A 96% degree of incorporation into the nanocapsules is confirmed.

EXAMPLE 4

Preparation of Nanocapsules Charged with Hydrophilic Active Agents Dressed Beforehand in Inverse Micelles Sodium fluorescein crystals are incorporated with heating at 50° C. and with stirring into a mixture of Labrafac containing inverse micelles of Span 80 (10% mass/mass).

After homogenization of this micellar suspension, 0.25 ml is introduced into the system described in Example 1, just before the chill-hardening step. The system is then in the form of a microemulsion obtained by phase inversion of a system emulsified via a thermal effect. A 75% degree of incorporation of sodium fluorescein into the final particles is measured by fluorescence spectroscopy.

EXAMPLE 5

Preparation of Nanocapsules Whose Lipid Core is Charged with a Water-Dispersible Active Principle The active agent, namely doxorubicin hydrochloride, is dressed beforehand in inverse micelles. To do this, 5 ml of inverse micelles (obtained by mixing 0.6 g of Span 80® with 3 g of Labrafac® under vortex stirring) are mixed with 2 mg of doxorubicin hydrochloride in powder form.

The mixture obtained above is incubated for 30 minutes at a temperature of 70° C. with magnetic stirring. The above mixture is then centrifuged for 5 minutes (13 400 rpm) in order to remove the excess undissolved doxorubicin hydrochloride.

1.934 g of Solutol HS 15®, 89 mg of sodium chloride, 846 mg of lipophilic Labrafac WL 1349® and 2.055 g of distilled water are mixed together with heating (90° C.) for 5 minutes with stirring (500 rpm). The mixture is then slowly cooled to 85° C.

1 ml of the inverse micellar suspension incorporating doxorubicin hydrochloride, obtained previously, is then added to this mixture, while increasing the stirring speed (700 rpm).

At 72° C., the above mixture is diluted with 12.5 ml of distilled water.

The same procedure is performed, this time adding 3 ml of inverse micelles incorporating doxorubicin hydrochloride (instead of 1 ml).

EXAMPLE 6

Physicochemical Characterization of Nanocapsules Charged with Doxorubicin Hydrochloride The physicochemical properties (size, polydispersity index PDI and zeta potential ZP) of control nanocapsules comprising, respectively, 1 ml and 3 ml of inverse micelles not charged with active agent, were compared with nanocapsules comprising, respectively, 1 ml and 3 ml of inverse micelles charged with doxorubicin hydrochloride, obtained according to Example 5.

The results are given in Tables I (control nanocapsules) and II (nanocapsules charged with active agent) below.

The polydispersity index (PDI) reflects the size distribution of the nanocapsules. A low PDI ($\leq 0.15$) indicates that the nanocapsules have a size distribution of Gaussian type, i.e. a size centered about a mean size value.

The zeta potential (ZP) indicates the repulsive force present at the surface of the nanocapsules and enables prediction of their long-term stability. Thus, if all the particles in suspension have a large negative or positive zeta potential, they tend to repel each other and cannot become assembled. On the other hand, if their zeta potential is low, no force prevents them from assembling together and thus being stable.

TABLE I

| Control nanocapsules | | | |
| --- | --- | --- | --- |
| Volume of inverse micelles (ml) | Size (nm) | PDI | ZP (mV) |
| 1 | 43.6 ± 0.7 | 0.04 ± 0.01 | −4.6 ± 2.9 |
| 3 | 86.1 ± 2.2 | 0.08 ± 0.02 | −8.8 ± 1 |

TABLE II

| Nanocapsules charged with doxorubicin hydrochloride | | | |
| --- | --- | --- | --- |
| Volume of inverse micelles charged with doxorubicin hydrochloride (ml) | Size (nm) | PDI | ZP (mV) |
| 1 | 43.5 ± 0.7 | 0.04 ± 0.01 | −5.9 ± 0.6 |
| 3 | 94.8 ± 6.0 | 0.13 ± 0.05 | −10.4 ± 1.2 |

It emerges from Tables I and II above that, for the same volume of added inverse micelles, no differences in sizes between nanocapsules containing control inverse micelles and inverse micelles charged with doxorubicin hydrochloride are observed, which confirms that the active agent is incorporated into the core of the nanocapsules in accordance with the present invention.

In addition, in both cases (control nanocapsules and nanocapsules charged with doxorubicin hydrochloride), the polydispersity index value is low, i.e. less than 0.15, and thus shows that the size distribution of the nanocapsules is narrow, i.e. centered about a mean size value.

Finally, in general, the measured zeta potentials are weakly negative and no significant difference is observed between the zeta potential of the nanocapsules containing doxorubicin hydrochloride and those not containing it (control). These low zeta potential values confirm the stability of the sample of nanocapsules obtained, in accordance with the preparation process according to the present invention.

EXAMPLE 7

Encapsulation Yield

The encapsulation yield (in %) of the nanocapsules obtained according to Example 5 was calculated and the results are given in Table III below.

The encapsulation yield (EY) corresponds to the proportion of doxorubicin hydrochloride encapsulated in the nanocapsules relative to the total doxorubicin hydrochloride added to the formulation.

More specifically, this yield is calculated according to the following formula (DOX=doxorubicin hydrochloride hereinbelow):

EY (%)=(amount of DOX in the nanocapsules×100)/ (amount of DOX in the nanocapsules+amount of free DOX).

Assay of the encapsulated doxorubicin hydrochloride is measured by spectrofluorimetry, using a Fluoroskan Ascent® spectrophotometer from Thermo Fisher Scientific (Cergy-Pontoise, France) which illuminates the sample at an excitation wavelength $\lambda_1$ ($\lambda_1$=485 nm) and which measures the optical density at an emission wavelength $\lambda_2$ ($\lambda_2$=550 nm).

TABLE III

| Size of the nanocapsules (nm) | Encapsulation yield (%) | Standard deviation |
| --- | --- | --- |
| 45 | 37.3 | 5.87 |
| 90 | 54.0 | 7.86 |

From the above results, the encapsulation yield is dependent on the size of the nanocapsule. For a mean size of 90 nm, more than half of the doxorubicin hydrochloride is incorporated into the nanocapsules obtained according to the process of the present invention.

EXAMPLE 8

Release Kinetics

The rate of release of doxorubicin hydrochloride was measured in order to evaluate the stability of the nanocapsules obtained in Example 5.

The rate of release of the doxorubicin hydrochloride was evaluated by spectrofluorimetry assay of the doxorubicin hydrochloride released using a Fluoroskan Ascent® spectrophotometer from Thermo Fisher Scientific (Cergy-Pontoise, France) which illuminates the sample at an excitation wavelength $\lambda_1$ ($\lambda_1$=485 nm) and which measures the optical density at an emission wavelength $\lambda_2$ ($\lambda_2$=550 nm).

Figure 2:
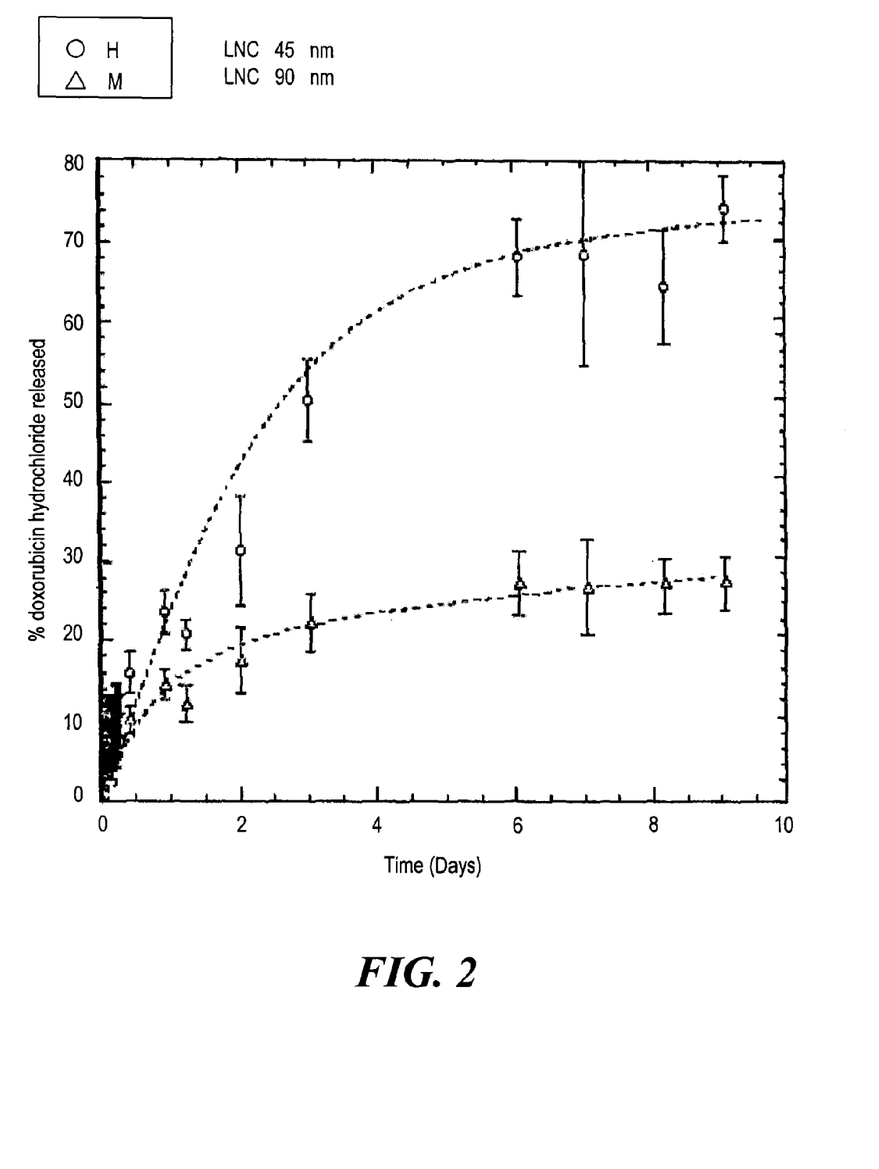
FIG. 2 shows the amount of doxorubicin hydrochloride released from nanocapsules (pH 7.4 and at 37° C.), as a function of time (days). The term "LNC" therein means "lipid nanocapsule".

FIG. 2 indicates the percentage of release of doxorubicin hydrochloride as a function of time (charged nanocapsules at pH 7.4; 37° C.).

It emerges from FIG. 2 that the degradation of the nanocapsules and thus the release of the doxorubicin hydrochloride from the nanocapsules is slow over time. Specifically, about 70% of the doxorubicin hydrochloride is released from nanocapsules 45 nm in size after 7 days and about 26% of this active agent is released from nanocapsules 90 nm in size after 7 days.

More specifically, the release profile is different according to the size of the nanocapsules: the larger the nanocapsules, the slower and more spread out over time the release profile.

Such release kinetics demonstrate that the nanocapsules obtained according to the preparation process of the present invention have a slow degradation profile and are stable.

EXAMPLE 9

Lyophilization of the Nanocapsules

The nanocapsules obtained according to Example 5 are subjected to a standard lyophilization process, in order to evaluate their sturdiness.

The lyophilization process is performed according to the methods well known to those skilled in the art, using a Lyovac-GP2 lyophilizer coupled to a Unistat 385 cryothermostat. The lyophilization is entirely performed at a pressure of 0.01 mbar. The system is maintained at a temperature of −45° C. for one hour and rises to a temperature of 15° C. over 5 hours. It is maintained for 2 hours at a temperature of 15° C. and passes to a temperature of 25° C. over 2 hours.

The results are given in Table IV below:

TABLE IV

| Volume of the inverse micelles charged with | Before lyophilization | | After lyophilization | |
| --- | --- | --- | --- | --- |
| DOX (ml) | size (nm) | PDI | size (nm) | PDI |
| 1 | 43.5 ± 0.7 | 0.04 ± 0.01 | 51.0 ± 4.4 | 0.2 ± 0.04 |
| 3 | 94.8 ± 6.0 | 0.13 ± 0.05 | 129.4 ± 23.7 | 0.19 ± 0.02 |

From the results indicated in Table IV, a small change in the size of the nanocapsules before and after lyophilization is observed, thus showing the sturdiness of the nanocapsules obtained via the process according to the present invention. In particular, the polydispersity index remains correct after lyophilization, thus confirming the stability of the nanocapsules obtained via the process according to the present invention.

Thus, the physicochemical characteristics of the nanocapsules obtained according to the preparation process of the present invention are stable and show good conservation properties.

The invention claimed is:

1. A process for preparing nanocapsules by incorporating an active agent inside at least one of a liquid lipid core or a solid lipid shell of the nanocapsule, the process comprising:
   contacting a microemulsion with a second oily composition under conditions suitable for promoting the incorporation of the active agent inside nanodroplets of an oily phase of the microemulsion; and
   chill-hardening the microemulsion charged with the active agent in order to obtain nanocapsules comprising the active agent,
   wherein the microemulsion is formulated by phase inversion of an emulsion through a phase inversion temperature operation, the microemulsion is free from the active agent, the microemulsion is stabilized with a surfactant system comprising a hydrophilic, nonionic, heat-sensitive surfactant, the second oily composition is totally or partially formed from the active agent to be charged, in which the second oily composition is different than the microemulsion, the active agent is either: (i) liposoluble or lipodispersible, or (ii) water-soluble or water-dispersible and in the form of inverse micellar species with a surfactant having an HLB value of less than 10, the nanocapsules have a lipid core that is liquid at room temperature, coated with a lipid shell that is solid at room temperature, and the water-soluble or water-dispersible active agent in the form of inverse micellar species, or the liposoluble or lipodispersible active agent, is incorporated inside the liquid lipid core, the solid lipid shell, or both, of the nanocapsules.

2. The process according to claim 1, wherein the surfactant system further comprises a liposoluble surfactant.

3. The process according to claim 2, wherein the liposoluble surfactant comprises a phospholipid.

4. The process according to claim 2, wherein the liposoluble surfactant is a lecithin comprising phosphatidylcholine in an amount of from 40% to 80% by weight.

5. The process according to claim 1, wherein the microemulsion undergoes a phase inversion temperature operation after interacting with the second compositiona.

6. The process according to claim 1, wherein the phase inversion operation comprises:

increasing the temperature of the microemulsion, optionally charged with an active agent, up to a temperature $T_2$ above its phase inversion temperature (PIT) to obtain a water-in-oil emulsion, followed by decreasing the temperature to a temperature $T_1$, wherein $T_1 < PIT < T_2$, to again obtain an oil-in-water emulsion, optionally, performing a temperature cycle around the phase inversion zone between $T_1$ and $T_2$ and stabilizing the system at a temperature that is in or close to the phase inversion zone to form a new microemulsion obtained via phase inversion.

7. The process according to claim 1, wherein the microemulsion is formulated by temperature-mediated phase inversion of an oil-in-water emulsion stabilized with the surfactant system.

8. The process according to claim 1, wherein the microemulsion comprises an oily fatty phase formed from a liquid or semiliquid fatty substance.

9. The process according to claim 8, wherein the oily fatty phase comprises a medium-chain triglyceride.

10. The process according to claim 8, wherein the
surfactant system further comprises a liposoluble surfactant, and
a liquid fatty substance/liposoluble surfactant ratio is from 1 to 15.

11. The process according to claim 8, wherein the oily fatty phase comprises a triglyceride, a fatty acid ester, or a mixture thereof.

12. The process according to claim 11, wherein the fatty acid ester is a $C_8$ to $C_{18}$ fatty acid ester.

13. The process according to claim 1, wherein the hydrophilic surfactant has a hydrophilic-lipophilic balance of from 10 to 18.

14. The process according to claim 1, wherein the hydrophilic surfactant is at least one selected from the group consisting of an ethoxylated fatty alcohol, an ethoxylated fatty acid, a partial glyceride of an ethoxylated fatty acid, a fatty acid triglyceride, and an ethoxylated derivative thereof.

15. The process according to claim 1, wherein the microemulsion comprises a fatty acid triglyceride, a polyethylene glycol 2-hydroxystearate derivative, and, optionally, a lecithin.

16. The process according to claim 1, wherein the nanocapsules have a solid shell thickness of from 2 to 10 nm.

17. The process according to claim 1, wherein the active agent is incorporated into the shell of the nanocapsules.

18. The process according to claim 1, wherein the active agent is incorporated into the core of the nanocapsules.

19. The process according to claim 1, wherein the second oily composition comprises at least one selected from the group consisting of a triglyceride and a fatty acid ester.

* * * * *